United States Patent [19]

Araki et al.

[11] Patent Number: 5,015,786
[45] Date of Patent: May 14, 1991

[54] PREPARATION OF CUMENE THROUGH ALKYLATION OF AN AROMATIC COMPOUND AND PREPARATION OF PHENOL THROUGH CUMENE

[75] Inventors: Shintaro Araki, Ichihara; Fujihisa Matsunaga, Wakayama; Hiroshi Fukuhara, Ichihara, all of Japan

[73] Assignee: Mitsui Petrochemical Industries Inc., Tokyo, Japan

[21] Appl. No.: 441,477

[22] Filed: Nov. 27, 1989

[30] Foreign Application Priority Data

Nov. 28, 1988 [JP] Japan .................. 63-300300
Nov. 30, 1988 [JP] Japan .................. 63-302617
Dec. 12, 1988 [JP] Japan .................. 63-328722

[51] Int. Cl.$^5$ .................. C07C 37/07; C07C 39/04
[52] U.S. Cl. .................. 568/798; 568/362; 568/385; 568/754; 568/768; 568/862; 585/446
[58] Field of Search .............. 585/446; 568/569, 573, 568/798, 754, 768, 846, 862, 880; 586/385, 362, 754, 768, 798

[56] References Cited

U.S. PATENT DOCUMENTS

| | | | |
|---|---|---|---|
| 4,238,417 | 12/1980 | Austin et al. | 568/385 |
| 4,267,380 | 5/1981 | Austin et al. | 568/385 |
| 4,268,454 | 5/1981 | Pez et al. | 568/880 |
| 4,567,304 | 1/1986 | Fulmer | 568/385 |
| 4,783,559 | 11/1988 | Matsushita et al. | 568/862 |
| 4,877,909 | 10/1989 | Mizusaki et al. | 568/880 |

FOREIGN PATENT DOCUMENTS

| | | | |
|---|---|---|---|
| 0164568 | 12/1985 | European Pat. Off. | 568/385 |
| 0025653 | 5/1974 | Japan | 568/385 |
| 0073796 | 6/1980 | Japan | 568/385 |

*Primary Examiner*—Werren B. Lone
*Attorney, Agent, or Firm*—Nixon & Vanderhye

[57] ABSTRACT

In a first form, a process is provided for preparing phenol by converting acetone by-produced by the cumene process into isopropanol, and alkylating benzene with the isopropanol and optional propylene, thereby forming phenol without acetone by-product. And cumene is prepared by alkylating benzene in the presence of a zeolite catalyst using isopropanol or a mixture of isopropanol and propylene as an alkylating agent. Further provided is the continuous alkylation of benzene with isopropanol wherein a reaction mixture is divided into first and second portions, with the first portion being recycled to the reactor and the second portion being taken out as a reaction product.

7 Claims, 1 Drawing Sheet

F I G. 1

PREPARATION OF CUMENE THROUGH ALKYLATION OF AN AROMATIC COMPOUND AND PREPARATION OF PHENOL THROUGH CUMENE

This invention relates to the preparation of cumene by alkylating an aromatic compound, the preparation of phenol via cumene, and the alkylation of an aromatic compound using an alcohol as the alkylating agent.

BACKGROUND OF THE INVENTION

Alkylated aromatic compounds obtained by alkylating aromatic compounds are commercially important intermediate stock materials. For example, cumene obtained by reacting benzene with propylene is a very important compound as a reactant for the synthesis of phenol.

Cumene is generally produced by alkylating benzene with propylene. Numerous studies have been made on this alkylation process. For example, Japanese Patent Application Kokai No. 40419/1982 discloses alkylation under liquid phase conditions using Lewis acid catalysts. U.S. Pat. No. 2,375,724 discloses the use of solid phosphoric acid catalysts.

Cumene is also produced by alkylating benzene with isopropanol. Reaction under gas phase conditions using solid acids is well known as disclosed in Japanese Patent Application Kokai No. 159427/1983 and 159430/1983. Reaction under liquid phase conditions has also been proposed. For example, U.S. Pat. No. 4,011,278 discloses alkylation in the presence of an H-mordenite catalyst having a silica-to-alumina ratio adjusted to 40.

These processes for the synthesis of cumene have several problems. For example, the alkylation using Lewis acids needs the presence of alcohols because the catalysts are readily deactivated by water in the reaction system, and alkylation with alcohols is impossible. The gas phase alkylation with isopropanol is substantially impractical because of low alkylation conversion and quick deterioration of the catalyst which must be frequently regenerated to compensate for such a short lifetime. The liquid phase alkylation with isopropanol is high in alkylation conversion, but is doubtful about its practical effectiveness because the percent yield of the end product is not demonstrated. This process has left a problem to be overcome for commercial production because expensive catalysts such as ZSM-5 zeolite having a high silica-to-alumina ratio and dealuminated H-mordenite are used for water repellency.

It is well known in the prior art to react benzene with propylene to produce cumene, to oxidize cumene to produce cumene hydroperoxide, and to acid cleave cumene hydroperoxide into phenol and acetone. A conventional phenol preparing process having these steps combined is generally known as the cumene or cumol-phenol process.

It is also an old well-known technique to hydrogenate acetone into isopropanol. This technique is still widely used at present for the assay of the catalytic activity of a hydrogenating catalyst and other purposes. For example, the activity of Raney nickel catalysts is often examined by comparing their acetone hydrogenating ability. Several advanced processes have been proposed as disclosed in Japanese Patent Application Kokai Nos. 12729/1987 and 7338/1987.

For the alkylation of benzene with isopropanol, reaction under gas phase conditions using solid acids is well known as disclosed in Japanese Patent Application Kokai Nos. 159427/1983 and 159430/1983. Reaction under liquid phase conditions is also proposed as disclosed in U.S. Pat. No. 4,011,278.

As to the reuse of the acetone which is by-produced in the cumene process, for example, by its conversion into isopropanol, no useful proposals have been made.

The phenol preparing process generally known as the cumene process is characterized by the production of acetone by-product, which is advantageous from some aspects, but disadvantageous from other aspects. More particularly, it is an advantage in that simultaneous production of two products in a single preparation unit is more efficient than individual production in separate units. In turn, if the proportion of phenol and acetone produced is unbalanced relative to their commercial demands, one for less demand is produced largely in vain.

As is known in the art, acetone is available in surplus for these years. Thus the production of acetone by-product is now considered as a serious drawback of the cumene process. Although acetone has found the majority of its application as a starting material for preparing methyl methacrylate, the demand for acetone is decreasing because of a switch of the starting material for preparing methyl methacrylate to another.

Under the circumstances, there is a need for the development of a phenol preparing process which is devoid of production of acetone and other by-products. Although several proposals have been made, there is available no process capable of preparing phenol in satisfactory yields.

In addition, impurities in propylene often cause a drawback during the preparing step of cumene from benzene and propylene in the cumene process for the preparation of phenol. That is, propylene for use in the cumene preparation is manufactured generally using crude oil as the starting material. Crude oil, however, contains sulfur compounds and various heavy metals, and these impurities are sometimes carried in propylene as trace contaminants during its manufacturing process. For example; carbonyl sulfide (COS) as a sulfur compound or As as a heavy metal contaminant in propylene inhibits function of a catalyst (aluminum chloride-HCl complex) for use in the cumene preparation, thus disturbing normal progress of the cumene synthesis. Therefore, a strict purification process is perproduced to avoid contamination of propylene with these impurities. Types and quantity of these contaminants, however, vary depending on not only the crude oil source but also the difference in the process conditions for the preparation of propylene from crude oil. Such irregularity burdens the propylene purification process with exceptionally complex and severe steps.

In consequence, a process for the preparation of propylene with highly stable purity containing no such impurities has been expected to be established, for the purpose of reducing the extreme burden of steps in the propylene purification process.

As to the alkylation of aromatic compounds, a variety of processes are known in the art. For example, the alkylating process using olefins has been widely used in the industry, becoming one of the important industrial techniques. Various proposals have also been made on the alkylating process using alcohols.

Several prior art techniques for the alkylation of aromatic compounds using alcohols are described below. (1) Japanese Patent Application Kokai No.

159430/1983 discloses a process for preparing a 1,4-dialkylbenzene compound in the presence of an oxide-modified zeolite catalyst.

(2) Japanese Patent Application Kokai No. 263934/1986 discloses a process for preparing p-xylene by alkylating toluene with methanol in the presence of a ZSM-5 type zeolite catalyst.

(3) Japanese Patent Application Kokai No. 216128/1983 and 159427/1983 disclose processes for preparing a monoalkylbenzene or dialkylbenzene by reacting benzene or alkylbenzene with an alcohol in the presence of a proton-exchanged mordenite type zeolite catalyst.

(4) U.S. Pat. No. 4,011,278 discloses a process for alkylating various aromatic compounds with alcohols in the presence of a ZSM-5 type zeolite catalyst.

All these processes intend to increase the percent yield of the end alkyl aromatic compound by improving the catalyst.

It is generally difficult for the alkylation of aromatic compounds to selectively produce a desired compound. More particularly, alkylated products are usually more reactive to the alkylation than starting reactants so that further alkylation may proceed to form higher alkylated products, providing a bar against the selective alkylation. For this reason, a number of proposals have been made to achieve selective alkylation by improving the catalyst.

In the alkylation of aromatic compounds, the reactivity depends on the acidic nature and shape of the catalyst used. It is generally believed that the acidic nature of catalyst controls the reaction rate and the catalyst shape controls the selectivity.

It is to be noted that alkylation using alcohols yields water. In general, catalysts having acidic nature weaken their acidity in the presence of water. Even a loss of catalytic activity can occur particularly when the catalysts used are solid acids. Thus in the event that water can form, various measures have been taken including the use of severe reaction conditions for increased reactivity and the use of water-resistant catalysts.

However, the selectivity of the desired compound is reduced under such severe reaction conditions or in the presence of improved catalysts, for example, modified strongly acidic catalysts, because highly alkylated products are formed or dehydration of alcohols results in olefin by-products.

For the alkylation of aromatic compounds using alcohols as the alkylating agent as described above, no commercial technique capable of selective production of a desired reaction product has been completed.

SUMMARY OF THE INVENTION

Therefore, one object of the present invention is to provide a novel and improved process for preparing phenol in commercially acceptable yields without forming a by-product.

The problem of the cumene process is the by-production of acetone in large amounts rather than the low yield of phenol. The inventors have solved the problem by converting the by-produced acetone into isopropanol, alkylating benzene with the isopropanol, and using supplemental propylene for alkylation along with isopropanol if the available isopropanol runs short. Combining these steps, the inventors have completed a process for preparing phenol without forming an acetone by-product.

Moreover, cumene synthesized by using isopropanol which has been converted from acetone by means of hydrogenation does not contain any of the sulfur compounds and heavy metals which are contained in the alkylation process of benzene using propylene which is manufactured generally using crude oil as the starting material.

In one form of the present invention, the object can be attained by properly combining the following steps of:

(a) alkylating benzene with isopropanol and/or propylene to synthesize cumene, (b) oxidizing the cumene from step (a) into cumene hydroperoxide, (c) subjecting the cumene hydroperoxide to acid cleavage to synthesize phenol and acetone, and (d) hydrogenating the acetone from step (c) into isopropanol which is recycled to step (a).

The process in the first form of the invention ensures that only phenol be prepared from benzene, oxygen and hydrogen by way of compounds having 3 carbon atoms.

Another object of the present invention is to provide a novel and improved process for preparing cumene in high yields and with a minimum amount of by-products using isopropanol.

In a second form of the present invention, there is provided a process for preparing cumene comprising alkylating benzene with an alkylating agent in the presence of a zeolite catalyst wherein the alkylating agent is isopropanol or a mixture of isopropanol and propylene.

Preferably, the zeolite is a proton-exchanged Y type skeleton zeolite having a ratio of silica to alumina of from 4/1 to less than 10/1.

A further object of the present invention is to provide a process for the alkylation of benzene with isopropanol whereby an end product can be synthesized with an increased selectivity.

In a third form, the present invention provides a method for the alkylation of benzene with isopropanol in a reactor, comprising the steps of: dividing a reaction mixture containing olefins from the reactor into two portions A and B, recycling portion A to the reactor again along with a fresh alkylating reactant in the same amount as portion B, and taking the remaining portion B out of the reaction system as a reaction product mixture.

BRIEF DESCRIPTION OF THE ACCOMPANYING DRAWING

The only figure, FIG. 1 schematically illustrates a reaction system suited in the practice of the present invention.

DETAILED DESCRIPTION OF THE INVENTION

The phenol preparing process according to the first form of the present invention is typically represented as a continuous process comprising the following steps.

```
┌─(a-1)-(b)-(c)-(d) ─┐

┌─(a-2)-(b)-(c)-(d) ─┐
```

```
    (a-3)-(b-2)-(c)-(d)
         └─ (a-4) ─┘
```

Steps (a) through (d) involved in the process will be described in detail.

Step (a)

Step (a) is a step for alkylating benzene to synthesize cumene.

Although benzene alkylating step (a) is classified into steps (a-1), (a-2), a-3), and (a-4) in the practice of the invention, the alkylating agent used in these benzene alkylating steps may be propylene alone, isopropanol alone, or a mixture of propylene and isopropanol.

First, the use of the alkylating agent predominantly comprising isopropanol (including the alkylating agent consisting of isopropanol) will be described.

In preparing cumene by alkylating benzene with isopropanol and supplemental propylene, a solid acidic substance is used as the catalyst. The useful catalysts include ordinary solid acids such as activated earth, silica, and silica-alumina, metal oxides such as titanium oxide, zinc oxide, and zirconium oxide, various zeolites which draw attention as the shape selective catalyst in these years, and compounds in which these zeolites are modified with metal ions. Among these catalysts, zeolites are preferred. The alkylation of benzene with isopropanol and supplemental propylene may be carried out under either gas or liquid phase conditions. The reaction temperature preferably ranges from 100° to 450° C., more preferably from 150° to 300° C. The reaction atmosphere may be under reduced, atmospheric or increased pressure although pressurizing is necessary to maintain the liquid phase if liquid phase reaction is desired.

The molar ratio of benzene to isopropanol preferably ranges from 20/1 to 1/10, more preferably from 5/1 to 2/1. When propylene is additionally used, the preferred molar ratio of benzene to isopropanol to propylene is such that the molar ratio of those having 3 carbon atoms (isopropanol plus propylene) to benzene ranges from 20/1 to 1/10, more preferably from 5/1 to 2/1 and the molar ratio of isopropanol to propylene ranges from 3/1 to 1/100, more preferably from 5/1 to 1/10.

In the practice of the invention, the alkylation of benzene with isopropanol may be carried out in either a batchwise or continuous manner. Since solid catalysts can be used in different forms, a fluidized bed system may be employed for powder catalysts and a fixed bed system may be employed for granular catalysts. The use of a fixed bed system is preferred for ease of separation of the reaction product from the catalyst and the simplicity of the reactor.

In this form of alkylation reaction, some higher alkylated products and water are formed as by-products in addition to the end product, cumene. Thus, the reaction mixture resulting from alkylation is subjected to fractional distillation, separating into unreacted propylene, unreacted benzene, cumene, higher alkylated products, and water. The unreacted benzene and higher alkylated products are recycled to the alkylation step for further alkylation.

Secondly, the alkylation predominantly using propylene will be described.

The alkylation of benzene predominantly using propylene (inclusive of the only use of propylene) may be the alkylation step of the well-known cumene process. The catalyst for reaction between benzene and propylene is typically an aluminum chloride complex which may be prepared by causing aluminum chloride to absorb hydrogen chloride gas in a solvent such as cumene.

The molar ratio of benzene to propylene preferably ranges from 1/1 to 10/1, more preferably from 1.2/1 to 6/1. The aluminum chloride complex catalyst is preferably added in an amount of 0.01 to 5% by weight, more preferably 0.1 to 1% by weight of aluminum chloride. In this reaction, hydrogen chloride gas may be co-present in the reaction system in order to stabilize the complex catalyst.

The alkylation to form cumene may be carried out at a temperature of 30° to 200° C., preferably 60° to 160° C. under a pressure of from atmospheric pressure to 15 kg-f/cm$^2$. The reaction may be effected in a batchwise, semi-batchwise, or continuous manner.

In this form of alkylation reaction, some higher alkylated products and water are formed as by-products in addition to the end product, cumene. Thus, the reaction mixture resulting from alkylation is subjected to fractional distillation, separating into unreacted propylene, unreacted benzene, cumene, higher alkylated products, and water. The unreacted benzene and higher alkylated products are recycled to the alkylation step for further alkylation.

Step (b)

Step (b) is a step for oxidizing the cumene from step (a) to convert the cumene into cumene hydroperoxide.

Oxidation of cumene represented as step (b) or (b-2) in the process of the invention may be carried out at a temperature of 60° to 150° C., preferably 90° to 130° C. under a pressure of 1 to 10 kg/cm$^2$ using molecular oxygen. The molecular oxygen is available as oxygen gas, air, or a mixture of oxygen diluted with an inert gas. In order that the oxidation proceed smoothly, an alkaline compound may be added to the reaction system to adjust the pH of the system to an optimum level in the range of 8.5 to 10.5. The alkaline compound used includes aqueous solutions of sodium carbonate, potassium carbonate and potassium hydroxide. The alkaline compound may be added in small amounts at intervals during the progress of oxidation so as to maintain the optimum pH of the reaction system throughout the process. The reaction time required for this oxidation is not particularly limited, but may be selected so as to achieve the maximum selectivity of the end product or cumene hydroperoxide.

An initiator is preferably added to the reaction system to smoothly start oxidation. Examples of the initiator includes azo compounds such as $\alpha,\alpha'$-azobisisobutyronitrile and $\alpha,\alpha'$-azobiscyclohexylnitrile. The cumene hydroperoxide resulting from oxidation of cumene is also a preferred initiator. The initiator is preferably added to the system in an amount of from about 0.1 to 5% by weight, more preferably from about 0.5 to 2% by weight based on the reactants.

The oxidation may be carried out in a batchwise, continuous, or semi-batchwise manner.

Step (c)

Step (c) is a step for acid cleaving cumene hydroperoxide into phenol and acetone.

The cumene hydroperoxide is often present in a concentration of about 20 to 30% by weight in the reaction mixture resulting from step (b). The reaction mixture should preferably be concentrated, as by distillation, so as to increase the cumene hydroperoxide concentration to 60 to 85% by weight before the mixture is subject to acid cleavage. Such concentration may be carried out at a temperature of up to 150° C., preferably up to 100° C. Concentration at too higher temperatures would undesirably cause thermal decomposition of cumene hydroperoxide resulting in a low yield of the end product or phenol. As long as effective concentration is achieved, the temperature is preferably as low as possible for safe handling of the peroxide.

An acidic compound is used as the catalyst in the cleavage of step (c). The catalysts used herein include strong acids such as sulfuric acid, hydrochloric acid, and hydrofluoric acid. Also included are heteropolyacids such as phosphotungstic acid and phosphomolybdic acid. Solid acids such as ion-exchange resins and silica-alumina may also be used. The catalyst is preferably added in an amount of about 0.01 to 5% by weight, more preferably 0.1 to 2% by weight based on the reaction mixture concentrate.

Also, the acid cleavage uses a solvent as reaction medium. Examples of the solvent include aromatic hydrocarbons such as benzene, toluene, xylene, and cumene; aliphatic hydrocarbons such as hexane, heptane, cyclohexane, and methylcyclohexane; alcohols such as methanol, ethanol, propanol, and butanol; ketones such as acetone, methyl ethyl ketone, and methyl isobutyl ketone; and ethers such as diisopropyl ether and dibutyl ether. Acetone is the most preferred reaction medium because it is produced by the acid cleavage of cumene hydroperoxide. The amount of the solvent used is preferably about 1 to 20 times, more preferably about 2 to 10 times the weight of the reaction mixture concentrate undergoing acid cleavage.

The acid cleavage may be carried out in either a continuous or semi-batchwise manner. Batchwise operation is less desirable because a high concentration cumene hydroperoxide solution can come in contact with the acid catalyst, giving rise to too rapid cleavage.

At the end of acid cleavage, the reaction mixture is subject to concentration to recover the acetone. Part of the recovered acetone is used as the reaction medium for acid cleavage again while the remaining acetone corresponding to the amount produced by acid cleavage of cumene hydroperoxide is delivered to subsequent step (d) for hydrogenating acetone into isopropanol. The concentrate which has been stripped of acetone is subject to precision distillation for recovering the end product or phenol.

Step (d)

Step (d) is a step for hydrogenating the acetone of step (c) into isopropanol which is recycled to step (a).

Catalysts, often Raney nickel catalysts are used in the step of hydrogenating acetone into isopropanol. Also useful are nickel group catalysts such as reduced nickel catalyst which is reduced by reduction of oxidated nickel supported on kieselguhr, alumina, silica or the like; copper group catalysts such as copper-chromium, Raney nickel-copper, copper-zinc; and platinum group catalysts such as platinum, palladium, ruthenium, rhodium, and similar metals on active carbon, aluminum and other carriers, these catalysts are known as hydrogenating catalysts. The reaction temperature may range from room temperature to 200° C. For a commercially acceptable reaction rate, the reaction temperature may range from 60° to 150° C.

Too high reaction temperatures are undesired for economy because excessive hydrogenation of acetone is triggered resulting in reduced yields of isopropanol. Hydrogenation may be carried out by either liquid or gas phase reaction. Thus the pressure may range from atmospheric pressure to 80 kg/cm$^2$, more preferably from 5 to 50 kg/cm$^2$. Hydrogen gas is used relative to the acetone reactant in a molar ratio of from $\frac{1}{2}$ to 10/1, preferably from 1/1 to 5/1.

The hydrogenation may be carried out in the presence or absence of a reaction medium. Examples of the solvent used herein include alcohols such as methanol, ethanol, propanol, and butanol. Also useful is isopropanol which is the hydrogenation product of acetone. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic solvents may also be used, for example, dimethylformamide, dimethylacetamide, acetonitrile, and dimethyl sulfoxide. Also useful are saturated hydrocarbons such as hexane, heptane, cyclopentane, and cyclohexane. In the practice of hydrogenation, water is also preferred as the solvent.

The hydrogenation step may be batchwise or continuous. Depending on the shape of a particular catalyst used, reaction may be carried out in a fluidized bed using powder catalysts or a fixed bed using granular catalysts. Fixed bed reaction is preferred for ease of separation of the catalyst from the reaction mixture and simplicity of the reactor.

When hydrogenation of acetone is carried out in a fixed bed, hydrogen gas may be contacted with the reaction mixture in either gas-liquid counter flow or gas-liquid parallel flow. The liquid and gas flows may be used in either of liquid down flow-gas up flow, liquid up flow-gas up flow, and liquid down flow-gas down flow modes. To increase reaction rate, the liquid-gas down flow mode known as a trickle bed is preferred.

If desired, the isopropanol resulting from step (d) may be taken out of the system as a product without recycling to step (a).

The process of the invention having combined steps (a), (b), (c), and (d) as mentioned above can produce phenol in a reasonable yield from benzene by way of compounds having 3 carbon atoms without paying attention to the demand for acetone which is otherwise formed as a by-product by the conventional cumene process.

In the second form, the present invention provides a process for preparing cumene by alkylating benzene with isopropanol or a mixture of isopropanol and propylene. The invention uses a zeolite catalyst for this benzene alkylation reaction. The catalyst is preferably a proton-exchanged Y type skeleton zeolite having a ratio of silica to alumina in the range of from 4/1 to less than 10/1, more preferably from 5/1 to less than 8/1. The catalyst may be in either powdery or granular form.

The molar ratio of isopropanol to benzene preferably ranges from 1/10 to 10/1, more preferably from 2/1 to 5/1. When a mixture of isopropanol and propylene is used as the alkylating agent, the molar ratio of isopropanol/propylene mixture to benzene preferably ranges from 1/10 to 10/1, more preferably from 2/1 to 5/1, with the molar ratio of propylene to isopropanol ranging up to 1/1, more preferably up to 2/10.

The reaction temperature preferably ranges from 150° to 350° C., more preferably from 220° to 250° C.

The reaction atmosphere may be under reduced, atmospheric or increased pressure although pressurizing is necessary to maintain the liquid phase in carrying out liquid phase reaction. In the practice of the invention, the alkylation of benzene may be carried out in either a batchwise or continuous manner. With regard to the catalyst form, a fluidized bed system may be employed for powder catalysts whereas a fixed bed system may be employed for granular catalysts. The use of a fixed bed system is preferred for ease of separation of the reaction product from the catalyst and the simplicity of the reactor.

The percent yield of alkylation may be defined by the following expressions separately for different charges, that is, depending on whether the charge is isopropanol or an isopropanol/propylene mixture.

Yield of alkylation = (cumene + 2 × diisopropylbenzene + 3 × triisopropylbenzene)/isopropanol charge × 100 (%)

Yield of alkylation = (cumene + 2 × diisopropylbenzene + 3 × triisopropylbenzene)/(isopropanol charge + propylene charge) × 100 (%)

Now, the third form of the present invention will be described. Though having long engaged in the alkylation of aromatic compounds with alcohols, the inventors could not find the optimum reaction conditions for the efficient production of alkylated products. The inventors have found that one of the reasons why alkylated products could not be produced in high yields is the dehydration of alcohols simultaneous with the primary alkylation reaction. Olefins are formed by dehydration of alcohols. In fact, it was found that much olefins were dissolved in the reaction solution where reaction had formed an alkylated product in low yields.

Besides, it is also known to use olefins as the alkylating agent for the alkylation of aromatic compounds. Searching for a measure by which the olefins which are obtained as by-products during the primary reaction are utilized for alkylation, the inventors have discovered the present invention.

In the third form of the invention, there is provided a method for the continuous alkylation of an aromatic compound "benzene" with an alkylating agent in the form of an alcohol "isopropanol" in a reactor, comprising the steps of: dividing a reaction mixture containing olefins from the reactor into first and second portions A and B such that the proportion of first portion to second portion (A/B) is larger than unity, recycling the first portion A to the reactor again, and taking the remaining second portion B out of the reaction system as a reaction product mixture.

This method allows the alcohol charged as the alkylating agent to be selectively consumed by alkylation reaction, with a minimized proportion of the alcohol being converted into olefins by the secondary reaction. Thus the percent yield of the alkylated product can be increased without any inconvenience.

Surprisingly, it has also been found that the desired monoalkylated product is obtained with a substantially increased selectivity since the proportion of higher alkylated products in the entire alkylated products is minimized.

Figure 1:
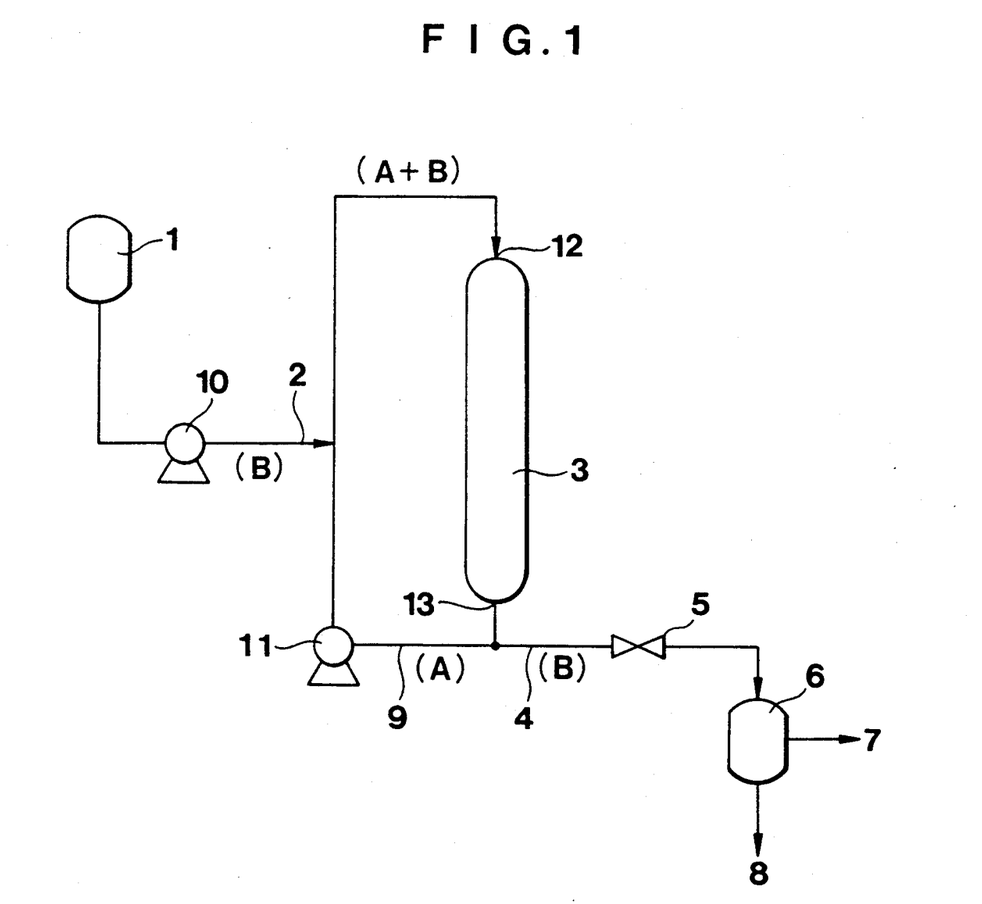

Referring to FIG. 1, there is schematically illustrated a reaction system for use in the practice of the method of the invention.

The reaction system shown in FIG. 1 includes a charge tank 1 containing an alkylating charge in the form of a mixture of an aromatic compound and an alcohol, a columnar reactor 3 connected to the charge tank 1 through a supply line 2, and an oil/water separator 6 connected to the reactor 3 through a product discharge line 4 and a pressure regulating valve 5 therein. The reactor 3 has top and bottom ports 12 and 13 in communication with each other through a recycle line 9. The supply line 2 is connected to the recycle line 9 adjacent the top port 12, and the discharge line 4 is connected to the recycle line 9 adjacent the bottom port 13. The supply line 2 includes a feed pump 10 for pumping the charge solution. The recycle line 9 includes a recycle pump 11 for recycling the reaction solution.

The reactor 3, which is filled with a solid catalyst as will be described later, receives at the top port 12 the charge from the supply line 2 and a portion of the reaction solution emanating from the bottom port 13 of the reactor and flowing through the recycle line 9. The reaction solution taken out of the bottom port 13 of the reactor is divided into two portions. The first portion is recycled to the reactor through the recycle line 9. The second portion is delivered through the discharge line 4 to the oil/water separator 6 where it is separated into a reaction product 7 and formed water 8 which are then taken out of the system.

To initiate the reaction, the reaction charge is introduced into the reactor 3 and the recycle line 9 connecting the reactor's top and bottom ports 12 and 13. The recycle pump 11 is driven to pump a portion of the reaction solution outgoing from the reactor bottom port 13 to the top port 12 again. The solution in the reactor 3 is continuously circulated through the recycle line 9 in this way. The flow of the first portion of the reaction solution through the recycle line 9 past the recycle pump 11 is regulated to a flow rate A. The reactor 3 is adjusted to predetermined conditions while continuing to recycle the reaction solution. When the reaction conditions have reached the predetermined conditions under which alkylation reaction takes place, the feed pump 10 is actuated to start feeding the alkylating charge in the form of a mixture of an aromatic compound and an alcohol in the tank 1 to the reactor 3 through the supply line 2 and the recycle line 9. The flow of the alkylating charge is regulated to a flow rate B. Then the flows through the supply and recycle lines 2 and 9 sum to a total flow of (A+B) to the reactor 3. Since the reactor 3 has been filled with the solution at the start of reaction, the additional supply of the alkylating charge to the reactor causes the reactor interior to be pressurized, giving rise to a pressure rise. Then the pressure regulating valve 5 in the discharge line 4 is opened to withdraw a portion of the reaction solution so as to maintain the reactor interior at the predetermined pressure. The second portion of the reaction solution diverted to the discharge line 4 is regulated to a flow rate equal to the flow rate B of the alkylating charge.

Then the object of the present invention is attained by controlling the pumps and valve such that the ratio of flow rate A to B may fall within a predetermined range.

The method of the invention will be described in more detail.

In the practice of the invention, a solid catalyst is used. The useful catalysts are generally acidic solid substances including silica-alumina, activated earth, zeolites, strongly acidic ion-exchange resins, and metal oxides. The zeolite catalysts include oxide-modified zeolites, ZSM-5 type zeolites, proton-exchanged mordenite type zeolites, Y type zeolites, US-Y type zeolites, and those zeolites further modified with metal ions. Examples of the useful metal oxide include oxides of iron, cobalt, nickel, chromium, and similar metals, and oxides of titanium and zirconium, as well as oxides of vanadium, niobium, antimony, and similar metals.

The catalyst used herein may be in either powder or granular form although granular catalysts are preferred for ease of separation of the reaction mixture from the catalyst.

The reaction temperature preferably ranges from 100° to 350° C., more preferably from 150° to 300° C. The reaction pressure is not particularly limited insofar as it is sufficient to maintain the reactor interior in liquid phase.

In the practice of the invention, the flow rate A of the first portion of the reaction solution recycled through the reaction system relative to the flow rate B of the freshly fed alkylating charge (which is equal to the flow rate of the second portion of the reaction solution discharged from the reaction system) is critical. The ratio of A/B should be larger than unity, preferably in the range of from 2 to 100, most preferably from 2 to 50. The method of the invention becomes ineffective with an A/B ratio of up to 1, and barely effective with an A/B ratio of up to 2. No further improvement is achieved with an A/B ratio of more than 100, indicating the uneconomical use of a pump having an unnecessarily increased capacity.

The amount of the alkylating charge fed in the practice of the invention may range from 0.1 to 20 hr$^{-1}$, preferably 0.5 to 10 hr$^{-1}$ in LHSV.

In the practice of the invention, the alkylating charge is a mixture of an aromatic compound(s) and an alcohol(s). The molar ratio of aromatic compound to alcohol may range from 1/1 to 12/1, preferably from 2/3 to 8/1.

Among numerous combinations of alcohols and aromatic compounds, commercially most important is the alkylation of benzene with isopropanol.

In the practice of the invention, a solvent may be added to the mixture of an alcohol and an aromatic compound. The useful solvents are solvents inert to the relevant alkylation reaction. Examples include hydrocarbon solvents such as pentane, hexane, eptane, cyclopentane, and cyclohexane.

The method of the invention favors a continuous mode of reaction. The type of reactor for continuous reaction may be either a fluidized bed system with a powder catalyst or a fixed bed system with a granular catalyst.

EXAMPLE

Examples of the present invention are given below by way of illustration and not by way of limitation.

The following examples relate to the preparation of phenol.

EXAMPLE 1

Alkylation of benzene with isopropanol

A stainless steel vertical reactor column having an inner diameter of 25.4 mm (1 inch) and a length of 500 mm was charged at a mid-portion with 50 ml of US-Y type zeolite. The reactor was filled with a charge in the form of a mixture of benzene and isopropanol in a molar ratio of 5/1, the isopropanol being recycled from the hydrogenating step as will be described later. The reactor was heated. When a temperature of 230° C. was reached, the additional charge was supplied to the reactor at the bottom at a flow rate of 50 ml/hr. The reaction was continued for 15 hours while maintaining the reaction pressure at 25 kg/cm$^2$.

No gas evolution was noticed during the process. There was obtained a reaction product containing separated organic and aqueous phases. The organic phase of the reaction product was analyzed by gas chromatography, finding a conversion of isopropanol and propylene of 99.4%, a yield of cumene of 17.7%, a diisopropylbenzene (DIPB) yield of 0.7%, and a yield of alkylation based on isopropanol of 93.8%. The organic phase had 0.35% by weight of propylene dissolved therein.

Oxidation of cumene

A 500-ml stainless steel autoclave equipped with an air blowing tube, alkali feed port, sampling nozzle, thermometer sheath, reflux condenser, and intensive stirrer was charged with 120 grams of cumene, 30 grams of 5% sodium carbonate aqueous solution, and 0.5 grams of $\alpha,\alpha'$-azobisisobutyronitrile initiator. The air in the autoclave was purged with nitrogen, then the nitrogen pressure was processed 5 kg/cm$^2$ as a starting pressure. Heating was started with stirring the contents of the autoclave. When the interior temperature reached 110° C., air blowing was started. At the same time as the start of air blowing, the rpm of the stirrer was increased to ensure sufficient gas-liquid contact. Cumene was oxidized by blowing air at a rate of 30 l/hr. While the oxidation reaction continued, the reaction mixture was sampled out at intervals through the sampling nozzle to examine the pH of the reaction mixture. Small portions of 5% sodium carbonate aqueous solution were pumped to the reactor through the alkali feed port so as to maintain the reaction mixture at pH 9 to 10.

The reaction was terminated when 10 hours had passed since the start of air blowing. The reaction mixture was taken out of the autoclave and separated into oily and aqueous phases. The oily phase was analyzed by liquid chromatography to determine the content of cumene hydroperoxide, finding that the oily phase contained 26% by weight of cumene hydroperoxide.

Acid cleavage of cumene hydroperoxide

The oily phase resulting from oxidation of cumene was concentrated at a temperature of 100° C. and a vacuum of 160 mmHg, distilling off the unreacted cumene. The concentrating operation was stopped when the oily phase was concentrated by a factor of about 3. The oily phase then contained about 78% by weight of cumene hydroperoxide.

A 500-ml four-necked flask equipped with a stirrer, dropping funnel, thermometer sheath, and reflux condenser was charged with 150 ml of acetone and 2 grams of conc. sulfuric acid. The dropping funnel was charged with 100 grams of the cumene hydroperoxide concentrate. The flask was set in a water bath at a temperature of 80° C. to cause the acetone to continuously reflux with stirring the flask contents.

Under acetone reflux, the cumene hydroperoxide concentrate was added dropwise to the flask from the funnel. The rate of addition of the concentrate was adjusted while observing the amount of refluxing acetone. After the entire amount of the cumene hydroperoxide concentrate was added, the reaction was continued for a further 30 minutes. At the end of reaction, the reaction mixture was analyzed by liquid chromatography, finding that little cumene hydroperoxide was left, that is, a conversion of approximately 100%. It was found that phenol was produced in an amount corresponding to 95% of the converted cumene hydroperoxide.

Powder sodium carbonate was added to the reaction mixture to neutralize the sulfuric acid catalyst. The solids were removed from the neutralized reaction mixture by filtration and the filtrate was concentrated to recover acetone. The amount of acetone recovered contained the acetone charge plus 28.5 grams of acetone resulting from acid cleavage of cumene hydroperoxide.

Hydrogenation of acetone

A vertical stainless steel reactor tube having an inner diameter of 25.4 mm (1 inch) and a length of 500 mm was loaded at an intermediate with 50 grams (24 ml) of lumpy Raney nickel alloy (R-20L manufactured by Nikko Rika K.K.). The reaction tube was filled with water and then 20% caustic soda aqueous solution was slowly pumped into the tube to develop the Raney nickel catalyst. The reactor interior temperature rose because the catalyst development produced exothermic heat. The flow rate of the caustic soda solution was controlled such that the reactor interior temperature did not exceed 60° C. After 0.5 liters of the caustic soda solution was pumped, the feed was replaced by water to rinse the reactor filling. Rinsing was continued until the water outflow from the reactor became neutral. At the end of rinsing, the pump feed was replaced by isopropanol to fill the reactor therewith. Heating of the reactor was started.

When the interior temperature reached 125° C., reaction was commenced by feeding acetone and hydrogen into the reactor from its bottom at a flow rate of 19 g/hr. and 16 l/hr., respectively. The reactor was maintained at a pressure of 20 kg/cm$^2$.

The reaction mixture exiting the reactor at the top was separated into the reaction liquid and hydrogen gas by means of a gas-liquid separator. The reaction liquid and hydrogen gas were discharged at a flow rate of 18.9 g/hr. and 8.1 l/hr., respectively.

The reaction was continued while acetone and hydrogen were continuously fed. The resulting isopropanol was recycled to the alkylating step. At the end of 9-hour reaction, the reaction liquid and hydrogen gas were respectively analyzed by gas chromatography. It was found that 1% by weight of acetone remained in the reaction liquid and the remaining component consisted solely of isopropanol. Analysis of the gas discharge showed the presence of 0.73% of methane, 0.02% of ethane and 0.07% of propane. Reaction efficacy was calculated on the basis of these analytical results, finding an acetone conversion of 99.0% and an isopropanol yield of 98.7%.

The resulting isopropanol could be reused as the alkylating agent for the alkylation of benzene.

EXAMPLE 2

Alkylation of benzene with isopropanol and propylene

A stainless steel vertical reactor column having an inner diameter of 25.4 mm (1 inch) and a length of 500 mm was loaded at a mid-portion with 50 ml of US-Y type zeolite. The reactor was filled with a charge in the form of a mixture of benzene, isopropanol, and propylene in a molar ratio of 50/9/1 and heated. When a temperature of 230° C. was reached, the additional charge was supplied to the reactor at the bottom at a flow rate of 50 ml/hr. The reaction was continued for 15 hours while maintaining the reaction pressure at 25 kg/cm$^2$. No gas evolution was noticed during the process. There was obtained a reaction product containing separated organic and aqueous phases. The organic phase of the reaction product was analyzed by gas chromatography, finding a conversion of isopropanol and propylene of 99.4%, a yield of cumene of 16.9%, a DIPB yield of 4.2%, and a yield of alkylation based on isopropanol and propylene of 92.7%. The organic phase had 0.62% by weight of propylene dissolved therein.

Next, the following steps were carried out in the same manner as in Example 1.

Oxidation of cumene

Acid cleavage of cumene hydroperoxide

Hydrogenation of acetone

There was finally obtained a reaction solution having 1.0% by weight of acetone left therein, with the balance consisting solely of isopropanol. Analysis of the gas discharge showed the presence of 0.00% of methane, 0.00% of ethane and 0.01% of propane. Reaction efficacy was calculated on the basis of these analytical results, finding an acetone conversion of 99.0% and an isopropanol yield of 99.0%.

The resulting isopropanol could be reused as the alkylating agent for the alkylation of benzene.

EXAMPLE 3

Alkylation of benzene with propylene

A 1-liter glass autoclave equipped with a Teflon-coated agitating blade and a thermometer sheath was charged with 78 grams of benzene and aluminum chloride complex. The amount of aluminum chloride complex charged was 0.08 grams calculated as aluminum chloride, which corresponded to a molar ratio of aluminum chloride complex to propylene of 1/1000. The autoclave was immersed in an oil bath and the interior of the autoclave was maintained at a temperature of 100° C. with thorough stirring.

To the autoclave, 25.2 grams of propylene in gaseous state was admitted in increments. That is, the propylene was supplied over a period of about 90 minutes while the interior pressure of the autoclave was maintained at 3 kg-f/cm$^2$. The reaction was terminated at the end of propylene supply, and the reaction mixture was taken out of the autoclave. The reaction mixture was analyzed by gas chromatography to find that it contained 25.1% by weight of cumene, 13.3% by weight of meta-diisopropylbenzene, 7.4% by weight of paradiisopropylbenzene, and 7.9% by weight of triisopropylbenzene. The total yield of cumene, diisopropylbenzenes, and triisopropylbenzene was 99% based on the weight of the propylene feed.

The reaction mixture was separated by distillation into unreacted benzene, cumene, higher isopropylated products. The higher isopropylated products were fed back to the initial or alkylation step for transalkylation to convert them into cumene.

Using 120 grams of the resulting cumene, isopropanol was produced by following the same procedures of cumene oxidation, acid cleavage, and acetone hydrogenation as in Example 1. The resulting isopropanol could be reused as the alkylating agent for the alkylation of benzene as in Example 1.

It is thus demonstrated that phenol can be produced from benzene without producing an acetone by-product by combining a series of steps of:

(a) alkylating benzene with isopropanol and/or propylene to synthesize cumene, (b) oxidizing the cumene of step (a) into cumene hydroperoxide, (c) acid cleaving the cumene hydroperoxide into phenol and acetone, (d) hydrogenating the acetone of step (c) into isopropanol and recycling the isopropanol to step (a).

The following examples relate to the preparation of cumene.

EXAMPLE 4

A stainless steel vertical reactor column having an inner diameter of 25.4 mm (1 inch) and a length of 500 mm was loaded at a mid-portion with 50 ml of proton-exchanged Y type zeolite having a silica-to-alumina ratio of 7. The reactor was filled with a charge in the form of a mixture of benzene and isopropanol in a molar ratio of 5/1 and heated. When a temperature of 230° C. was reached, the additional charge was supplied to the reactor at the bottom at a flow rate of 50 ml/hr. The reaction was continued for 15 hours while maintaining the reaction pressure at 25 kg/cm$^2$. No gas evolution was noticed during the process. There was obtained a reaction product containing separated organic and aqueous phases. The organic phase of the reaction product at the end of 15-hour reaction was analyzed by gas chromatography, finding a conversion of isopropanol of 99.4%, a yield of cumene of 19.8%, a yield of diisoproplbenzene (DIPB) of 5.1%, and a yield of alkylation based on isopropanol of 97.4%.

EXAMPLE 5

A stainless steel vertical reactor column having an inner diameter of 25.4 mm (1 inch) and a length of 500 mm was loaded at a mid-portion with 50 ml of proton-exchanged Y type zeolite having a silica-to-alumina ratio of 7. The reactor was filled with a charge in the form of a mixture of benzene and isopropanol in a molar ratio of 3/1 and heated. When a temperature of 230° C. was reached, the additional charge was supplied to the reactor at the bottom at a flow rate of 50 ml/hr. The reaction was continued for 200 hours while maintaining the reaction pressure at 25 kg/c$^2$. No gas evolution was noticed during the process. There was obtained a reaction product containing separated organic and aqueous phases. The organic phase of the reaction product at the end of 15-hour reaction was analyzed by gas chromatography, finding a conversion of isopropanol of 99.7%, a yield of cumene of 21.5%, a DIPB yield of 11.8%, and a yield of alkylation based on isopropanol of 94.5%.

EXAMPLE 6

A stainless steel vertical reactor column having an inner diameter of 25.4 mm (1 inch) and a length of 500 mm was loaded at a mid-portion with 50 ml of proton-exchanged Y type zeolite having a silica-to-alumina ratio of 7. The reactor was filled with a charge in the form of a mixture of benzene, isopropanol, and propylene in a molar ratio of 50/9/1 and heated. When a temperature of 230° C. was reached, the additional charge was supplied to the reactor at the bottom at a flow rate of 50 ml/hr. The reaction was continued for 15 hours while maintaining the reaction pressure at 25 kg/cm$^2$. No gas evolution was noticed during the process. There was obtained a reaction product containing separated organic and aqueous phases. The organic phase of the reaction product at the end of 15-hour reaction was analyzed by gas chromatography, finding a conversion of isopropanol and propylene of 99.4%, a yield of cumene of 17.7%, a DIPB yield of 3.7%, and a yield of alkylation based on isopropanol and propylene of 93.8%. The organic phase had 0.3% by weight of propylene dissolved therein.

Comparative Example 1

Conventional H-mordenite was treated with 6N hydrochloric acid, obtaining a dealuminated mordenite catalyst having a silica-to-alumina ratio of 40.

A stainless steel vertical reactor column having an inner diameter of 25.4 mm (1 inch) and a length of 500 mm was loaded at a mid-portion with 50 ml of the catalyst. The reactor was filled with a charge in the form of a mixture of benzene and isopropanol in a molar ratio of 5/1 and heated. When a temperature of 230° C. was reached, the additional charge was supplied to the reactor at the bottom at a flow rate of 50 ml/hr. The reaction was continued for 15 hours while maintaining the reaction pressure at 25 kg/cm$^2$. No gas evolution was noticed during the process. There was obtained a reaction product containing separated organic and aqueous phases. The organic phase of the reaction product was analyzed by gas chromatography, finding a conversion of isopropanol of 9%, a yield of cumene of 16.3%, a DIPB yield of 4.5%, and a yield of alkylation based on isopropanol of 88.5%.

As is evident from the foregoing examples, the use of a zeolite catalyst ensures that cumene is prepared from benzene in high yields using isopropanol or a mixture of isopropanol and propylene as the alkylating agent.

The following examples relate to the alkylation of aromatic compounds.

EXAMPLE 7

A reaction system as shown in FIG. 1 was used. A stainless steel vertical reactor column having an inner diameter of 25.4 mm (1 inch) and a length of 500 mm was loaded at a mid-portion with 50 ml of US-Y type zeolite (TSZ351PAH1 manufactured by Toso K.K., noodle form having a diameter of 1.5 mm). The reactor was filled with benzene. The recycle pump was actuated to recycle the reaction solution at a flow rate of 700 ml/hr. With the reactor interior controlled to a temperature of 230° C. and a pressure of 25 kg-f/cm$^2$G, a reactant charge in the form of a mixture of benzene and isopropanol in a molar ratio of 5/1 was supplied to the reactor at a flow rate of 50 ml/hr. A portion of the reaction mixture was discharged at a flow rate corresponding to the flow rate of supplying the benzene/isopropanol mixture, through the discharge line branched from the recycle line adjacent the bottom of the reactor. The reaction was continued for 8 hours while continuously supplying the the benzene/isopropanol mixture.

The reaction mixture was discharged in an amount of 42.8 grams during the last one-hour period. Since this reaction mixture was a mixture of oily and aqueous phases, the oily phase was separated from the aqueous phase. The oily phase was analyzed by capillary gas chromatography, finding a conversion of isopropanol of 99.9% and a yield of alkylation based on isopropanol of 98.4%.

The alkylated products contained 21.8% of cumene, 3.3% of diisopropylbenzene, and 0.1% of triisopropylbenzene, indicating a cumene selectivity of 89.5%. The percent formation of a propylene by-product in this alkylation reaction was 0.7%.

Comparative Example 2

The procedure of Example 7 was repeated except that the recycle pump was not activated.

The results showed a conversion of isopropanol of 99.8% and a yield of alkylation based on isopropanol of 97.0%. The percent formation of a propylene by-product in this alkylation reaction was 2.6%.

The alkylated products contained 19.8% of cumene, 5.1% of diisopropylbenzene, and 0.2% of triisopropylbenzene, indicating a cumene selectivity of 83.4%.

EXAMPLE 8

The procedure of Example 7 was repeated except that the catalyst was replaced by H-mordenite type zeolite (TSZ-640 manufactured by Toso K.K.). The results showed a yield of alkylation based on isopropanol of 98.3%. The alkylated products contained cumene with a selectivity of 78.9%.

Comparative Example 3

The procedure of Example 8 was repeated except that the reaction solution was not recycled. The results showed a yield of alkylation of 87.6% and a cumene selectivity of 73.7%

EXAMPLE 9

The procedure of Example 7 was repeated except that the reaction charge was replaced by a mixture of benzene and isopropanol in a molar ratio of 3/1. The results showed a yield of alkylation of 96.0% and a cumene selectivity of 80.8%.

Comparative Example 4

The procedure of Example 9 was repeated except that the reaction solution was not recycled. The results showed a yield of alkylation of 85.4% and a cumene selectivity of 54.1%. Propylene was by-produced in an amount of 14.6% based on the isopropanol charged.

EXAMPLES 10-11

The procedure of Example 7 was repeated while the flow rate of the recycling portion of the reaction mixture was varied. The results are shown in Table 1 together with the results of Example 7 and Comparative Example 2.

TABLE 1

| Example | Recycle flow of reaction mixture, A (ml/hr) | Yield of alkylation (mol %) | Cumene selectivity (mol %) | A/B |
|---|---|---|---|---|
| CE2 | — | 97.0 | 83.4 | — |
| E10 | 360 | 97.4 | 84.7 | 7.2 |
| E7 | 700 | 98.4 | 89.5 | 14 |
| E11 | 1270 | 98.9 | 91.1 | 25.4 |

It is evident from Table 1 that the cumene selectivity increases as the proportion of the recycling portion of the reaction mixture increases.

The third form of the invention provides a method for the alkylation of an aromatic compound using an alcohol as the alkylating agent wherein a portion of the reaction product mixture was recycled whereby olefin by-products are fed back to the reactor for further alkylation. The yield of alkylation based on the alcohol is increased and the selectivity of a monoalkylated product among alkylated products is substantially increased.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing phenol, comprising the steps of:
   (a-1) alkylating benzene with isopropanol using a zeolyte catalyst at a temperature in the range of from 100° to 450° C. under liquid phase conditions at elevated pressure to synthesize cumene,
   (b) oxidizing the cumene from step (a-1) with molecular oxygen at a temperature in the range of from 60° to 150° C. into cumene hydroperoxide,
   (c) subjecting the cumene hydroperoxide to acid cleavage with an acidic compound selected from the group consisting of strong acids, heteropolyacids and solid acids to synthesize phenol and acetone, and thereafter
   (d) hydrogenating the acetone from step (c) with hydrogen gas at a temperature in the range of from 60° to 150° C. in a fixed bed under liquid phase conditions into isopropanol which is recycled to step (a-1).

2. A process for preparing phenol, comprising the steps of:
   (a-2) alkylating benzene with isopropanol and propylene by using a catalyst at a temperature in the range of from 100° to 450° C. under liquid phase conditions at elevated pressure to synthesize cumene,
   (b) oxidizing the cumene from step (a-2) with molecular oxygen at a temperature in the range of from 60° to 150° C. into cumene hydroperoxide,
   (c) subjecting the cumene hydroperoxide to acid cleavage with an acidic compound selected from the group consisting of strong acids, heteropolyacids and solid acids to synthesize phenol and acetone, and thereafter,
   (d) hydrogenating the acetone from step (c) with hydrogen gas at a temperature in the range of from 60° to 150° C. in a fixed bed under liquid phase conditions into isopropanol which is recycled to step (a-2).

3. A process for preparing phenol, comprising the steps of:
   (a-3) reacting benzene with propylene by using a zeolyte catalyst at a temperature in the range of from 30° to 200° C. under liquid phase conditions at elevated pressure to synthesize cumene,
   (b-2) oxidizing the cumene from step (a-3), step (a-4), or both with molecular oxygen at a temperature in the range of from 60° to 150° C. into cumene hydroperoxide,
   (c) subjecting the cumene hydroperoxide to acid cleavage with an acidic compound selected from the group consisting of strong acids, heteropolyacids, and solid acids to synthesize phenol and acetone,
   (d) hydrogenating the acetone from step (c) with hydrogen gas at a temperature in the range of from 60° to 150° C. in a fixed bed under liquid phase conditions into isopropanol, and (a-4) alkylating benzene with isopropanol or a mixture of isopropanol and propylene using a zeolyte at a temperature in the range of from 100° to 450° C. under liquid phase conditions at increased pressure to synthesize cumene which is recycled to step (b-2).

4. The process of claim 1 of 3 wherein said zeolite is a proton-exchanged Y type skeleton zeolite having a ratio of silica to alumina of from 4 to less than 10.

5. The process of claim 1, 2, or 3 wherein the molar ratio of benzene is isopropanol or a mixture of isopropanol and propylene ranges from 1:10 to 10:1.

6. The process of claim 1, 2 or 3 wherein the alkylation of benzene with isopropanol is carried out in a reactor by the steps of:
   (1) dividing a reaction mixture containing olefins from the reactor into first and second portions such that the proportion of first portion to second portion is larger than 1,
   (2) recycling the first portion to the reactor again, and
   (3) taking the remaining second portion out of the reaction system as a reaction product mixture, thereby increasing the percent yield of alkylation while minimizing formation of olefin by-products from isopropanol.

7. The process of claim 6, wherein the ratio of first portion to second portion ranges from 2:1 to 100:1.

* * * * *

UNITED STATES PATENT AND TRADEMARK OFFICE
CERTIFICATE OF CORRECTION

PATENT NO. : 5,015,786
DATED : May 14, 1991
INVENTOR(S) : ARAKI et al

It is certified that error appears in the above-identified patent and that said Letters Patent is hereby corrected as shown below:

Column 19, claim 4, line 1, change "1 of 3" to --1, 2, or 3--.

Column 19, claim 5, line 2, change "is" to --to--.

Signed and Sealed this

Thirteenth Day of September, 1994

Attest:

BRUCE LEHMAN

Attesting Officer      Commissioner of Patents and Trademarks